United States Patent
Kato et al.

(10) Patent No.: US 8,054,175 B2
(45) Date of Patent: Nov. 8, 2011

(54) PORTABLE TYPE INFORMATION TRANSMITTING SYSTEM, PORTABLE TYPE INFORMATION TRANSMITTING APPARATUS AND PORTABLE TYPE INFORMATION RECEIVING APPARATUS

(75) Inventors: Kazuo Kato, Chiba (JP); Akira Takakuka, Chiba (JP)

(73) Assignee: Seiko Instruments Inc. (JP)

( * ) Notice: Subject to any disclaimer, the term of this patent is extended or adjusted under 35 U.S.C. 154(b) by 1035 days.

(21) Appl. No.: 11/827,017

(22) Filed: Jul. 10, 2007

(65) Prior Publication Data

US 2008/0018456 A1  Jan. 24, 2008

(30) Foreign Application Priority Data

Jul. 18, 2006 (JP) ................. 2006-195463

(51) Int. Cl.
*G08B 1/08* (2006.01)

(52) U.S. Cl. ........... 340/539.12; 600/509; 600/523; 600/300; 600/301; 128/903; 702/173; 368/47; 368/10

(58) Field of Classification Search ........ 600/509, 600/523, 300, 301; 128/903; 702/173; 368/47, 368/10
See application file for complete search history.

(56) References Cited

U.S. PATENT DOCUMENTS

| 5,743,269 | A | 4/1998 | Okigami et al. | 128/706 |
|---|---|---|---|---|
| 7,057,551 | B1 * | 6/2006 | Vogt | 342/357.57 |
| 7,828,697 | B1 * | 11/2010 | Oberrieder et al. | 482/8 |
| 2005/0094495 | A1 | 5/2005 | Takada et al. | 368/47 |
| 2005/0288559 | A1 | 12/2005 | Feliss et al. | 600/300 |
| 2006/0094353 | A1 * | 5/2006 | Nielsen et al. | 455/17 |
| 2008/0097228 | A1 | 4/2008 | Aihara et al. | 600/490 |

FOREIGN PATENT DOCUMENTS

| DE | 10042101 | 2/2002 |
|---|---|---|
| EP | 0556823 | 8/1993 |
| GB | 2415786 | 1/2006 |
| JP | 2002082187 | 3/2002 |
| JP | 2002330930 | 11/2002 |
| JP | 2004340605 | 12/2004 |
| WO | 2006037007 | 4/2006 |

* cited by examiner

*Primary Examiner* — Daniel Wu
*Assistant Examiner* — Frederick Ott
(74) *Attorney, Agent, or Firm* — Adams & Wilks

(57) ABSTRACT

A portable type information transmitting apparatus has a bionic information measuring section that outputs bionic information in accordance with a detected bionic signal. A standard radio wave receiving section receives a standard radio wave including current time information. A time counting section counts time. A time correcting section corrects the time counted by the time counting section based on the standard radio wave received by the standard radio wave section. A transmission data generating section generates transmission data including first time information corresponding to the time counted by the time counting section and the bionic information from the bionic information measuring section. A data transmission section transmits the transmission data generated by the transmission data generating section.

10 Claims, 7 Drawing Sheets

PORTABLE TYPE INFORMATION TRANSMITTING SYSTEM, PORTABLE TYPE INFORMATION TRANSMITTING APPARATUS AND PORTABLE TYPE INFORMATION RECEIVING APPARATUS

BACKGROUND OF THE INVENTION

1. Field of the Invention

The present invention relates to an information transmitting system for transmitting bionic information or time information, a portable type information transmitting apparatus, and a portable type information receiving apparatus suitable for constructing the information transmitting system.

2. Description of the Prior Art

In a background art, there has been developed as a type of a portable electronic apparatus a radio wave timepiece for receiving a standard radio wave including a time code indicating current time and automatically correcting time in correspondence with the time code. For example, a radio wave timepiece described in JP-A-2002-082187 (paragraphs [0011] through [0020], FIG. 1) is constituted such that a standard radio wave transmitted from a transmitting station is received by a receiving antenna and a receiving circuit included in a main body of a wristwatch type radio wave timepiece and a deviation of time of the radio wave timepiece is corrected. The wristwatch type radio wave timepiece is restricted to a portable size, and therefore, there is a problem that the receiving antenna included in the main body of the radio wave timepiece is restricted to be equal to or smaller than a constant size, which makes it difficult to increase a receiving sensitivity.

On the other hand, as other portable type electronic apparatus, as described in Domestic Re-publication WO96/29005 (page 5 through page 15, FIG. 1 through FIG. 7), there has been developed a portable type heartbeat meter for mounting a chest band including a heartbeat detecting circuit and a heartbeat number calculating circuit and a heartbeat interval data transmitting circuit at the chest portion of the human body, receiving a heartbeat interval data transmitted from the chest band by a receiving antenna and a receiving circuit included in a main body of a wristwatch, and displaying a heartbeat number at the wristwatch.

When a heartbeat measuring function is going to be added to a radio wave timepiece, it is necessary to provide both receiving antennas and receiving circuits. In this case, when the'radio wave timepiece is going to be downsized to a wristwatch size, the receiving antennas are obliged to be downsized, and therefore, there is a problem of the deterioration of the receiving sensitivities. Further, a circuit scale of hardware is increased, and therefore, when the receiving sensitivities are increased, large spaces are needed not only for the antennas but also for a peripheral circuit, making downsizing of the apparatus difficult to achieve.

It is an object of the invention to provide a portable type information transmitting system, a portable type information transmitting apparatus, and a portable type information receiving apparatus that can be downsized and that are capable of transmitting and receiving information with accuracy and efficiency.

SUMMARY OF THE INVENTION

According to the invention, there is provided a portable type information transmitting system characterized in comprising portable type information transmitting means including bionic information measuring means for outputting bionic information in correspondence with a detected bionic signal, standard radio wave receiving means for receiving a standard radio wave including current time information, first time counting means for executing a time counting operation, first time correcting means for correcting time of the first time counting means based on the standard radio wave received by the standard radio wave receiving means, transmitting data generating means for generating a transmitting data including the time information provided from the first time counting means and the bionic information provided from the bionic information measuring means, and data transmitting means for transmitting the transmitting data, and portable information receiving means including data receiving means for receiving the transmitting data from the data transmitting means, second time counting means for executing a time counting operation, second time correcting means for correcting time of the second time counting means based on the time information included in the transmitting data received by the data receiving means, and notifying means for notifying the time counted by the second time counting means and a bionic data based on the bionic information included in the transmitting data.

On a side of the portable type information transmitting means, the bionic information measuring means outputs the bionic information in correspondence with the detected bionic signal, the standard radio wave receiving means receives the standard radio wave, the first time correcting means corrects the time of the first time counting means based on the standard radio wave received by the standard radio wave receiving means, the transmitting data generating means generates the transmitting data including the time information provided from the first time counting means and the bionic information provided from the bionic information measuring means, and the data transmitting means transmits the transmitting data.

On a side of the portable type information receiving means, the data receiving means receives the transmitting data from the data transmitting means, the second time correcting means corrects the time of the second time counting means based on the time information included in the transmitting data received by the data receiving means, and the notifying means notifies the time counted by the second time counting means and the bionic data in correspondence with the bionic information included in the transmitting data.

Here, there may be constructed a constitution in which the portable information transmitting means further includes mounting detecting means for detecting whether the bionic information measuring means is mounted to the body, wherein when the mounting detecting means detects that the bionic information measuring means is not mounted to the body, the standard radio wave receiving means receives the standard radio wave, and the first time correcting means corrects the time of the first time counting means based on the standard radio wave received by the standard radio wave receiving means.

Further, there may be constructed a constitution in which the portable information transmitting means further includes first storing means for storing first identification information, and the transmitting data generating means further generates a signal including the first identification information as the transmitting data, wherein the portable type information receiving means further includes second storing means for storing second identification information in correspondence with the first identification information, and identification information determining means for determining whether the first and the second identification information are brought into a predetermined relationship, and when the identification information determining means determines that the first and the second identification information are brought into the predetermined relationship, the second time correcting means corrects the time of the second time counting means based on the time information included in the transmitting data.

Further, there may be constructed a constitution in which when the identification information determining means determines that the first and the second identification information are brought into the predetermined relationship, the notifying means notifies the bionic data based on the bionic information included in the transmitting data.

Further, there may be constructed a constitution in which the portable type information transmitting means further includes country information generating means for generating country information based on the standard radio wave, and the transmitting data generating means further generates a signal including the country information of the transmitting data as the transmitting data, wherein the notifying means of the portable type information receiving means notifies the country information included in the transmitting data.

Further, according to the invention, there is provided a portable type information transmitting apparatus characterized in comprising bionic information measuring means for outputting bionic information in correspondence with a detected bionic signal, standard radio wave receiving means for receiving a standard radio wave including current time information, time counting means for executing a time counting operation, time correcting means for correcting time of the time counting means based on the standard radio wave received by the standard radio wave receiving means, transmitting data generating means for generating a transmitting data including the time information provided from the time counting means and the bionic information provided from the bionic information measuring means, and data transmitting means for transmitting the transmitting data to outside.

The bionic information measuring means outputs the bionic information in correspondence with the detected bionic signal, the standard radio wave receiving means receives the standard radio wave, the time correcting means corrects the time of the time counting means based on the standard radio wave received by the standard radio wave receiving means, the transmitting data generating means generates the transmitting data including the time information provided from the time counting means and the bionic information provided from the bionic information measuring means, and the data transmitting means transmits the transmitting data.

Here, there may be constructed a constitution in which the bionic information measuring means further includes mounting detecting means for detecting whether the bionic information measuring means is mounted to the body, when the mounting detecting means detects that the bionic information measuring means is not mounted to the body, the standard radio wave receiving means receives the standard radio wave, and the time correcting means corrects the time of the time counting means based on the standard radio wave received by the standard radio wave receiving means.

Further, there may be constructed a constitution further comprising storing means for storing identification information, wherein the transmitting data generating means further generates a signal including the identification information as the transmitting data.

Further, there may be constructed a constitution further comprising country information generating means for generating country information based on the standard radio wave, wherein the transmitting data generating means further generates a signal including the country information as the transmitting data.

Further, according to the invention, there is provided a portable type information receiving apparatus characterized in comprising data receiving means for receiving a transmitting data including at least current time information and bionic information, time counting means for executing a time counting operation, time correcting means for correcting time of the time counting means based on the time information included in the transmitting data received by the data receiving means, and notifying means for notifying the time counted by the time counting means and bionic data based on the bionic information included in the transmitting data.

The data receiving means receives the transmitting data from the data transmitting means, the time correcting means corrects the time of the time counting means based on the time information included in the transmitting data received by the data receiving means, and the notifying means notifies the time counted by the time counting means and the bionic data in correspondence with the bionic information included in the transmitting data.

Here, there may be constructed a constitution further comprising storing means for storing identification information, and identification information determining means for determining whether identification information included in the transmitting data and the identification information stored to the storing means are brought into a predetermined relationship, and when the identification information determining means determines that two of the identification information are brought into the predetermined relationship, the time correcting means corrects the time of the second time counting means based on the time information included in the transmitting data.

Further, there may be constructed a constitution in which when the identification information determining means determines that two of the identification information are brought into the predetermined relationship, the notifying means notifies the bionic data based on the bionic information included in the transmitting data.

Further, there may be constructed a constitution in which the notifying means notifies country information included in the transmitting data.

According to the portable type information transmitting system according to the invention, a system constituent element can be downsized, and the time information can further firmly be received to notify.

Further, according to the invention, the portable type information transmitting apparatus and the portable type information receiving apparatus preferable for constructing the system can be provided.

BRIEF DESCRIPTION OF THE DRAWINGS

A preferred form of the present invention is illustrated in the accompanying drawings in which.

DETAILED DESCRIPTION OF THE PREFERRED EMBODIMENTS

An explanation will be given of a portable type information transmitting system according to an embodiment of the invention as follows. According to the embodiment, there is pointed out an example of a portable type information transmitting system having a function as a heartbeat meter for measuring a heartbeat and a function as a radio wave timepiece for automatically correcting time based on a time code included in a standard radio wave signal.

Figure 1:
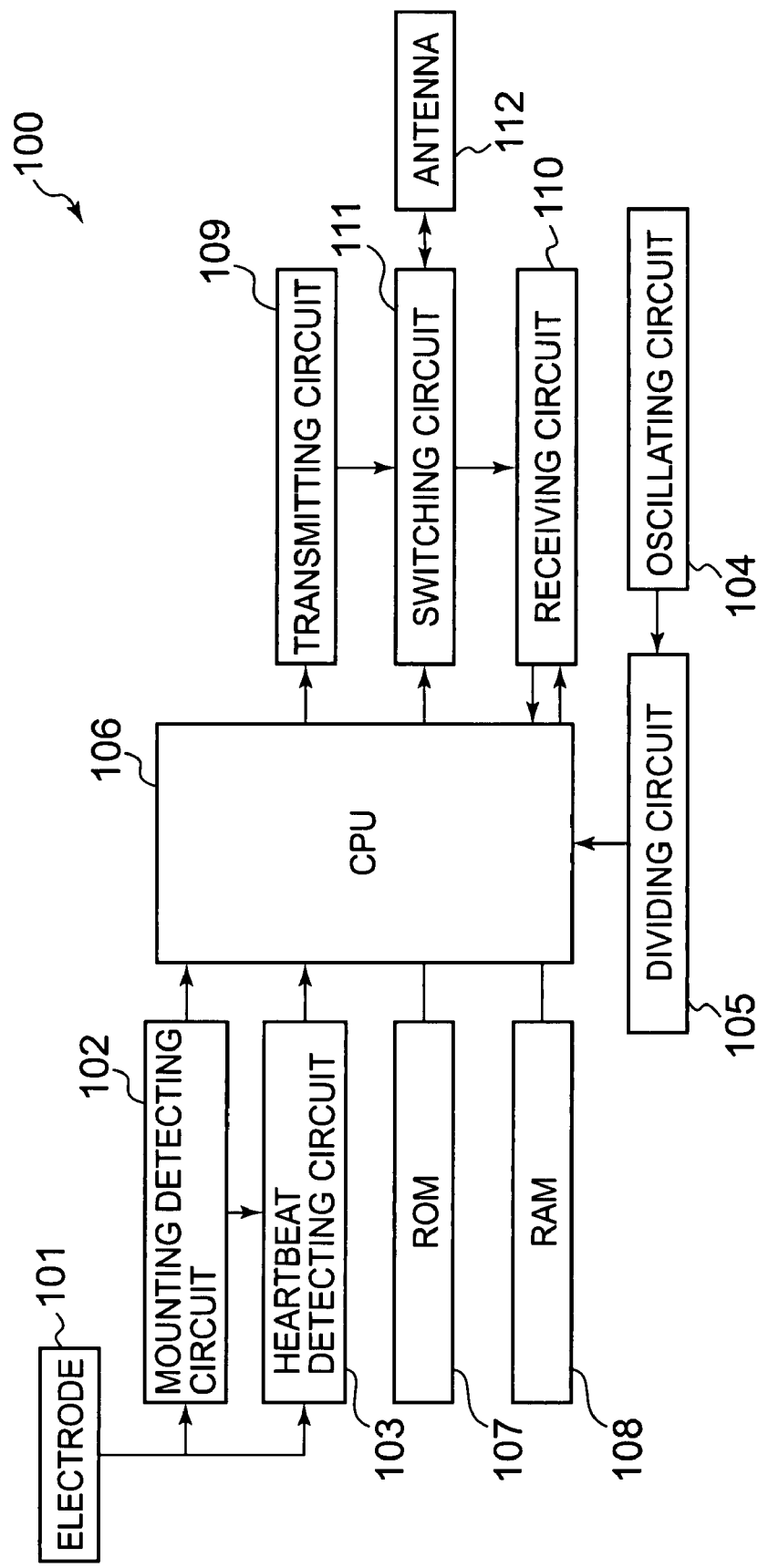
FIG. 1 is a block diagram of a portable type information transmitting apparatus used in a portable type information transmitting system according to a first embodiment of the invention.

FIG. 1 is a block diagram of a portable type information transmitting apparatus 100 used in a portable type information transmitting system according to a first embodiment of the invention. The portable type information transmitting apparatus 100 is provided with a heartbeat measuring function and a function as a radio wave timepiece and is of a chest band style used by being mounted to the chest of a measured person for measuring a heartbeat constituting a portable type information transmitting means.

In FIG. 1, the portable type information transmitting apparatus 100 includes an electrode 101 for detecting a heartbeat constituting a bionic signal and outputting a heartbeat signal in correspondence therewith, a mounting detecting circuit 102 for detecting whether the electrode 101 is mounted to the chest of a measured person, a heartbeat detecting circuit 103 for shaping a waveform of the heartbeat signal from the electrode 101 and outputting the heartbeat signal, and an oscillating circuit 104 for generating a signal at a predetermined frequency, a dividing circuit 105 for generating a clock signal constituting a reference of counting by dividing the signal generated by the oscillating circuit 104, a central processing unit (CPU) 106, a read only memory (ROM) 107 for storing a program or the like executed by CPU 106, a random access memory (RAM) 108 for storing data of heartbeat information, identification information or the like, a transmitting circuit 109, a receiving circuit 110, a switching circuit 111 for switching transmission and reception, and an antenna 112.

The antenna 112 is an antenna serving to receive a standard radio wave and to transmit a transmitting data including heartbeat information, current time information or the like. A frequency of the transmitting data is set to a frequency different from that of the standard radio wave.

Here, the electrode 101 and the heartbeat detecting circuit 103 constitute bionic information measuring means, the receiving circuit 110, the switching circuit 111 and the antenna 112 constitute standard radio wave receiving means, the oscillating circuit 104, the dividing circuit 105 and CPU 106 constitute first counting means, the transmitting circuit 109, the switching circuit 111 and the antenna 112 constitute data transmitting means, the mounting detecting circuit 102 constitutes mounting detecting means, and ROM 107 and RAM 108 constitute first storing means. Further, CPU 106 also constitutes first time correcting means, transmission data generating means for generating transmission data (hereinafter, "transmitting data generating means" and "transmitting data"), and country information generating means.

Figure 2:
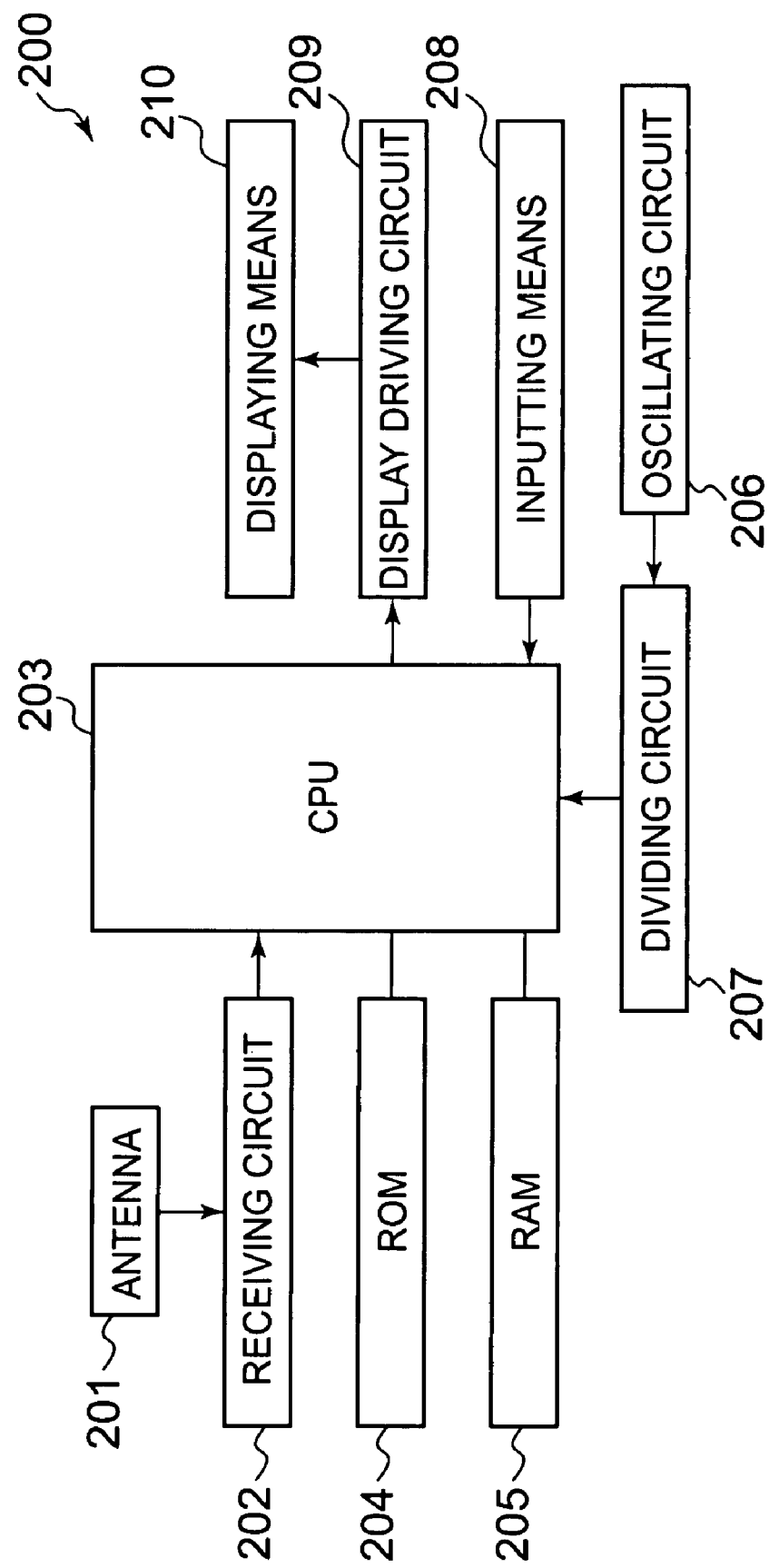
FIG. 2 is a block diagram of a portable type information receiving apparatus used in the portable type information transmitting system according to the first embodiment of the invention.

FIG. 2 is a block diagram of a portable type information receiving apparatus 200 used in the portable type information transmitting system. The portable type information receiving apparatus 200 is provided with a function of notifying the heartbeat information received from the portable type information transmitting apparatus 100 and a function of correcting time based on current time information received from the portable type information transmitting apparatus 100 and notifying current time, and is of a wristwatch style used by being mounted to the arm of the measured person for measuring a heartbeat to constitute portable type information receiving means.

In FIG. 2, the portable type information receiving apparatus 200 includes an antenna 201 for receiving a transmitting data from the portable type information receiving apparatus 100 by wireless, a receiving circuit 202 for outputting an information signal of the heartbeat information or the like included in the transmitting data received by the antenna 201, a central processing unit (CPU) 203, a read only memory (ROM) stored with a program or the like executed by CPU 203, a random access memory (RAM) 205 for storing a data of heartbeat information, identification information or the like, an oscillating circuit 206 for generating a signal at a predetermined frequency, a dividing circuit 207 for generating a clock signal constituting a reference of counting time by dividing the signal generated by the oscillating circuit 206, inputting means 208 constituted by a key switch or the like for operating to start to detect a heartbeat or the like, a display driving circuit 209, and displaying means 210 constituted by a liquid crystal display device (LCD) or the like.

A signal frequency receivable by the antenna 201 and the receiving circuit 202 is set to a frequency by which although the transmitting data from the information transmitting apparatus 100 can be received, the standard radio wave cannot be received.

Here, the antenna 201 and the receiving circuit 202 constitute data receiving means, CPU 203, the oscillating circuit 206 and the dividing circuit 207 constitute second counting means, the display driving circuit 209 and the displaying means 210 constitute notifying means, and ROM 204 and RAM 205 constitute second storing means. Further, CPU 203 constitutes also second time correcting means, identification information determining means.

Figure 3:
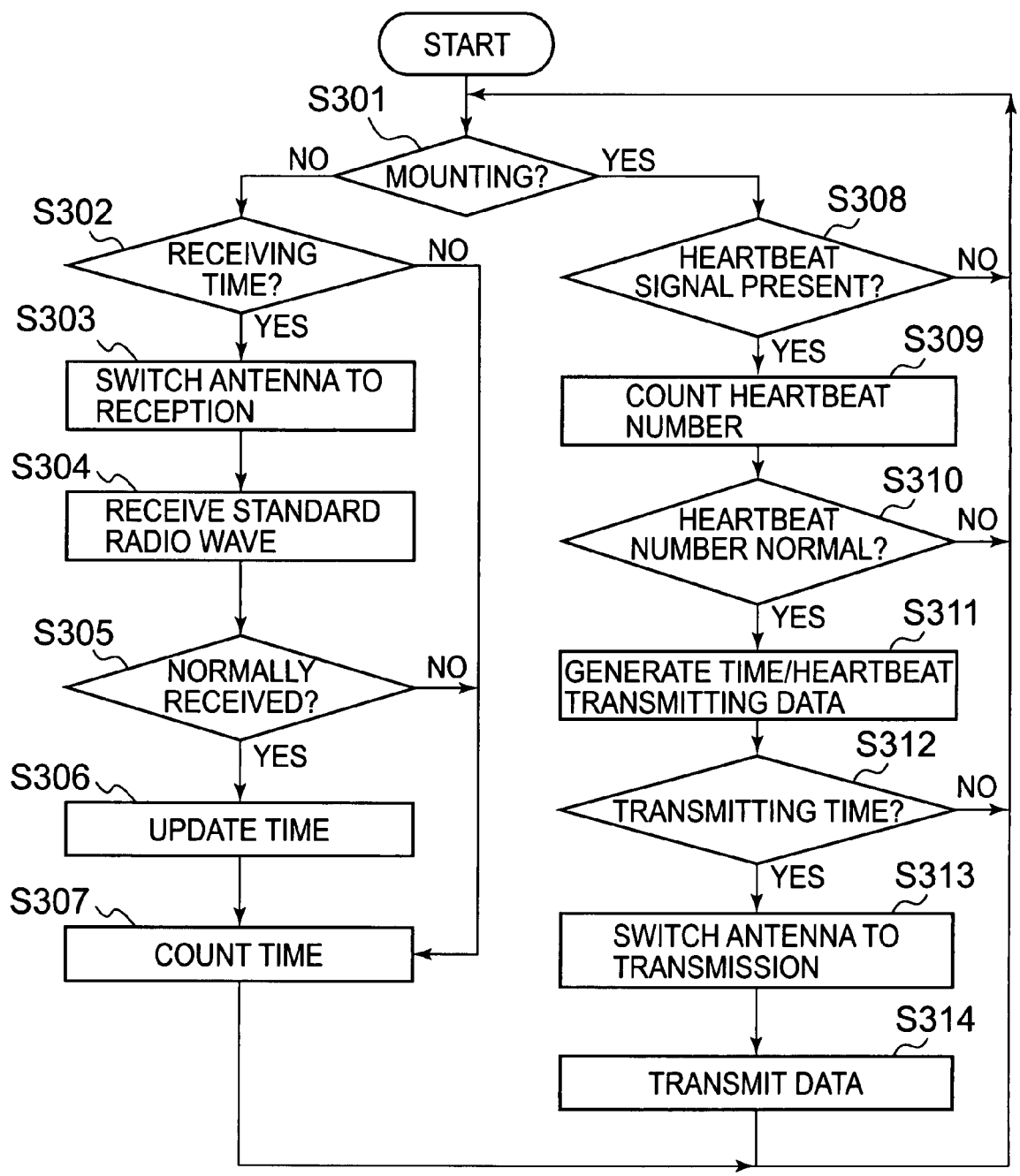
FIG. 3 is a flowchart showing a processing of the portable type information transmitting apparatus according to the first embodiment of the invention.

FIG. 3 is a flowchart showing a processing of the portable type information transmitting apparatus 100, and the processing is a processing carried out by CPU 106 by executing the program stored to ROM 107.

Figure 4:
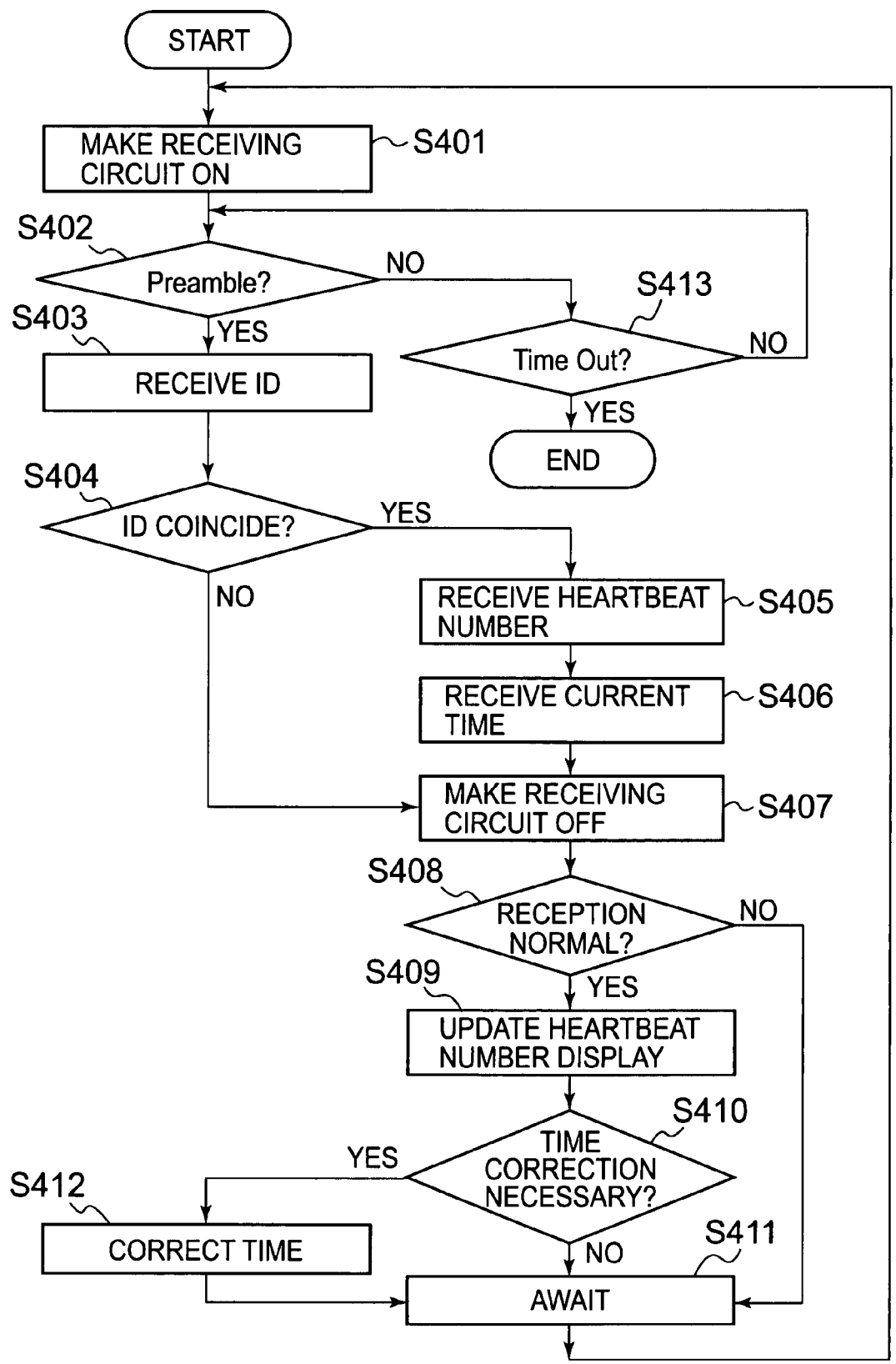
FIG. 4 is a flowchart showing a processing of the portable type information receiving apparatus according to the first embodiment of the invention.

FIG. 4 is a flowchart showing a processing of the portable type information receiving apparatus 200, and the processing is a processing carried out by CPU 203 by executing the program stored to ROM 204.

Figure 5:
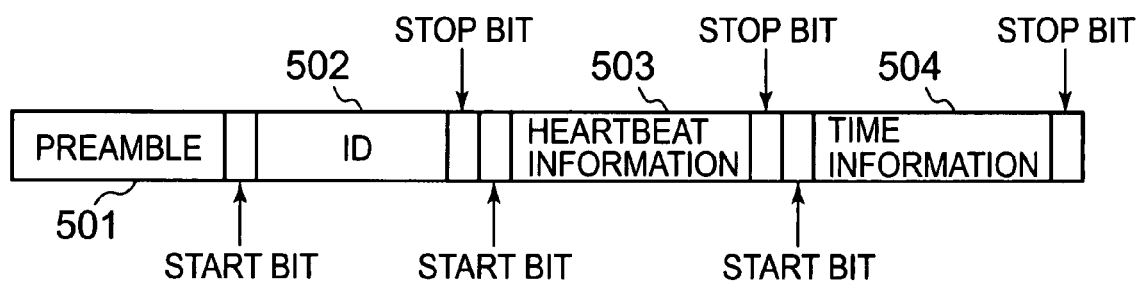
FIG. 5 is a diagram showing a style of a transmitting data used in the portable type information transmitting system according to the first embodiment of the invention.

FIG. 5 is a diagram showing a style of the transmitting data transmitted from the portable type information transmitting apparatus 100 to the portable type information receiving apparatus 200. In FIG. 5, the transmitting data includes a preamble 501, identification information (ID) 502, heartbeat information 503, time information 504 including year, month, date, and the respective information are interposed by start bits and stop bits.

As a method of setting the identification information 502, the identification information may be stored to RAM 108 in fabricating the portable type information transmitting apparatus 100, and identification information having a predetermined relationship with (for example, the same as) identification information from the inputting means 208 of the portable type information receiving apparatus 200 may be stored to RAM 205. In this case, as identification information, a serial number, a lot number or the like of a product may be used.

Further, as other setting method, the identification information may be stored to RAM 108 in fabricating the portable type information transmitting apparatus 100, or, a random number generated by CPU 106 may be stored to RAM 108, information the same as or in a predetermined relationship with identification information included in a transmitting data received first from the portable type information transmitting apparatus 100 may be stored to RAM 205 by the portable type information receiving apparatus 200 as identification information, and it may be determined whether the transmitting data is transmitting data to one's own address by using the identification information.

By including the inherent identification information in the transmitting data in this way, a cross talk with a signal of other apparatus can be prevented.

An explanation will be given of operation of the portable type information transmitting system according to the first embodiment in reference to FIG. 1 through FIG. 5 as follows.

The mounting detecting circuit 102 outputs a low level signal (body unmounting detecting signal) indicating that the body is not mounted therewith in a state in which the body of a user is not mounted with the portable type information transmitting apparatus 100 (specifically, the electrode 101) and outputs a high level signal (body mounting detecting signal) indicating that the body is mounted therewith in a state in which the body (specifically, the chest) of the measured person is mounted with the portable type information transmitting apparatus 100 (specifically, the electrode 101).

CPU 106 determines whether the body of the measured person is mounted with the information transmitting apparatus 100 based on a detecting signal from the mounting detecting circuit 102 indicating whether the body of the measured person is mounted with the portable type information transmitting apparatus 100 (step S301 of FIG. 3).

CPU 106 determines unmounting when a signal from the mounting detecting circuit 102 is an unmounting detecting signal and determines whether time of receiving the standard radio wave is reached (step S302), and when it is determined that the time is reached, CPU 106 switches a tuning circuit at inside of the switching circuit 111 to a circuit for reception and connects the antenna 112 to switch to a side of the receiving circuit 110 (step S303).

Next, CPU 106 receives the standard radio wave including a time code indicating the current time by way of the antenna 112, the receiving circuit 110 (step S304), when the time code is normally received (step S305), CPU 106 corrects counted time to the current time in correspondence with the time code (step S306), thereafter, carries out counting operation based on the clock signal from the diving circuit 105 (step S307).

CPU 106 proceeds to a processing step S307 without correcting time when it is determined that the time code cannot normally be received at the processing step S305.

Further, CPU 106 proceeds to the processing step S307 without carrying out the time correcting processing when it is determined that time for correcting time is not reached at the processing step S302.

On the other hand, CPU 106 determines that mounting has been finished when the signal from the mounting detecting circuit 102 is a mounting detecting signal at the processing step S301, determines whether the heartbeat signal is received by way of the electrode 101 and the heart beat detecting circuit 103 (step S308), and calculates the heartbeat number per minute based on the heartbeat signal detected in a predetermined time period when it is determined that the heartbeat signal is received (step S309).

Next, CPU 106 determines whether the calculated heartbeat number is a normal value (for example, determines as the normal value when the heartbeat number is a numerical value within a predetermined range) (step S310), in the case of the normal value, CPU 106 generates a transmitting data of the style shown in FIG. 5 by synthesizing the current time information, the heartbeat number information and the identification information stored to RAM 108 (step S311), when the transmission time period by a predetermined period is reached (step S312), CPU 106 switches the tuning circuit of the switching circuit 111 for transmission and connects the antenna 112 to switch to a side of the transmitting circuit 109 (step S313), and transmits output the transmitting data (step S314).

In this way, there is constructed a constitution of transmitting the transmitting data periodically by the predetermined period, and therefore, in comparison with the constitution of transmitting the transmitting data when specific time is reached, it is not necessary to determine that the specific time is reached, and therefore, the constitution can be simplified.

On the other hand, on a side of the portable information receiving apparatus 200 mounted to the one's own arm of the measured person, when a heartbeat display operation is operated to start by the inputting means 208, CPU 203 makes the receiving circuit 2020N in response thereto to start to receive the transmitting data from the information transmitting apparatus 100 (step S401 of FIG. 4).

CPU 203 receives the preamble 501 in the received signal (step S402), thereafter, receives the identification information 502 (step S403). When the received identification information is brought into a predetermined relationship with (for example, coincides with) identification information stored to RAM 205 (step S404), CPU 203 receives the heartbeat information and the current time information (steps S405, S406), thereafter, stops receiving operation by making the receiving circuit 202 OFF (step S407).

When CPU 203 determines that the received signal is normal based on the received heartbeat number information or the like (step S408), CPU 203 updates a heartbeat number display of the displaying means 210 to a display of the newly received heartbeat number (step S409).

Next, CPU 203 determines whether it is necessary to correct time counted by CPU 203 per se (step S410). Here, CPU 203 determines that it is necessary to correct time when a first transmitting data in starting the heartbeat detecting operation by operating the inputting means 208 is received. When CPU 203 determines that it is necessary to correct time, CPU 203 corrects the one's own counting time by the current time (step S412), thereafter, carries out the counting operation continuously based on the clock signal from the dividing circuit 207 and awaits for a predetermined time period (step S411), thereafter, returns to step S401 and makes the receiving circuit 2020N again and repeats the above-described processing. Thereby, a receiving operation in synchronism with the transmission period on the side of the information transmitting apparatus 100 can be carried out, and power consumption can be reduced.

When CPU 203 determines that it is not necessary to correct time at the processing step S410, CPU 203 proceeds to the processing step S411 without correcting time.

When CPU 203 does not determine that reception is carried out normally at the processing step S408, CPU 203 proceeds to the processing step S411 without carrying out the processing of updating the heartbeat number and the processing of correcting time.

When CPU 203 determines that the identification information is not brought into the predetermined relationship at the processing step S4.04, CPU 203 proceeds to step S407 without carrying out the receiving operation.

Further, when CPU 203 does not receive the preamble 501 for a predetermined time period at the processing step S402, CPU 203 finishes the processing (step S413).

As described above, according to the first embodiment, the portable type information transmitting apparatus 100 corrects time counted by the portable type information transmitting apparatus 100 per se based on the current time information included in a received standard radio wave, transmits information of the current time and information of measured heartbeat as the transmitting data, the portable type information receiving apparatus 200 corrects time counted by the portable type information receiving apparatus 200 per se based on the current time information included in the transmitting data and displays the current time and the heartbeat number information included in the transmitting data, and therefore, there is achieved the capability of carrying out reception with a sensitivity higher than that in the case of correcting time by receiving the standard radio wave by the antenna included in the radio timepiece of the background art.

Further, the style of the transmitting data is constituted by only adding the current time information to the style of the transmitting data used in the heartbeat detecting system of the background art (identification information+heartbeat information), and therefore, the side of the information receiving apparatus 200 may be constructed by a simple constitution of adding a processing a software, and the wristwatch added with the radio wave correcting function can be realized while the hardware stays to be the wristwatch having the heartbeat measuring function of the background art.

Further, an electric field intensity of a radio wave transmitted by the information transmitting apparatus 100 is stronger than that of the standard radio wave, and therefore, receiving sensitivities of the receiving antenna 201 and the receiving circuit 202 included in the information receiving apparatus 200 may be lower than a receiving sensitivity of the radio wave correcting timepiece of the background art, and therefore, there is achieved an effect of capable of carrying out stable operation.

Next, an explanation will be given of a portable type information transmitting system according to a second embodiment of the invention, a portable type information transmitting apparatus and a portable type information receiving apparatus preferable for constructing the portable type information transmitting system.

Figure 6:
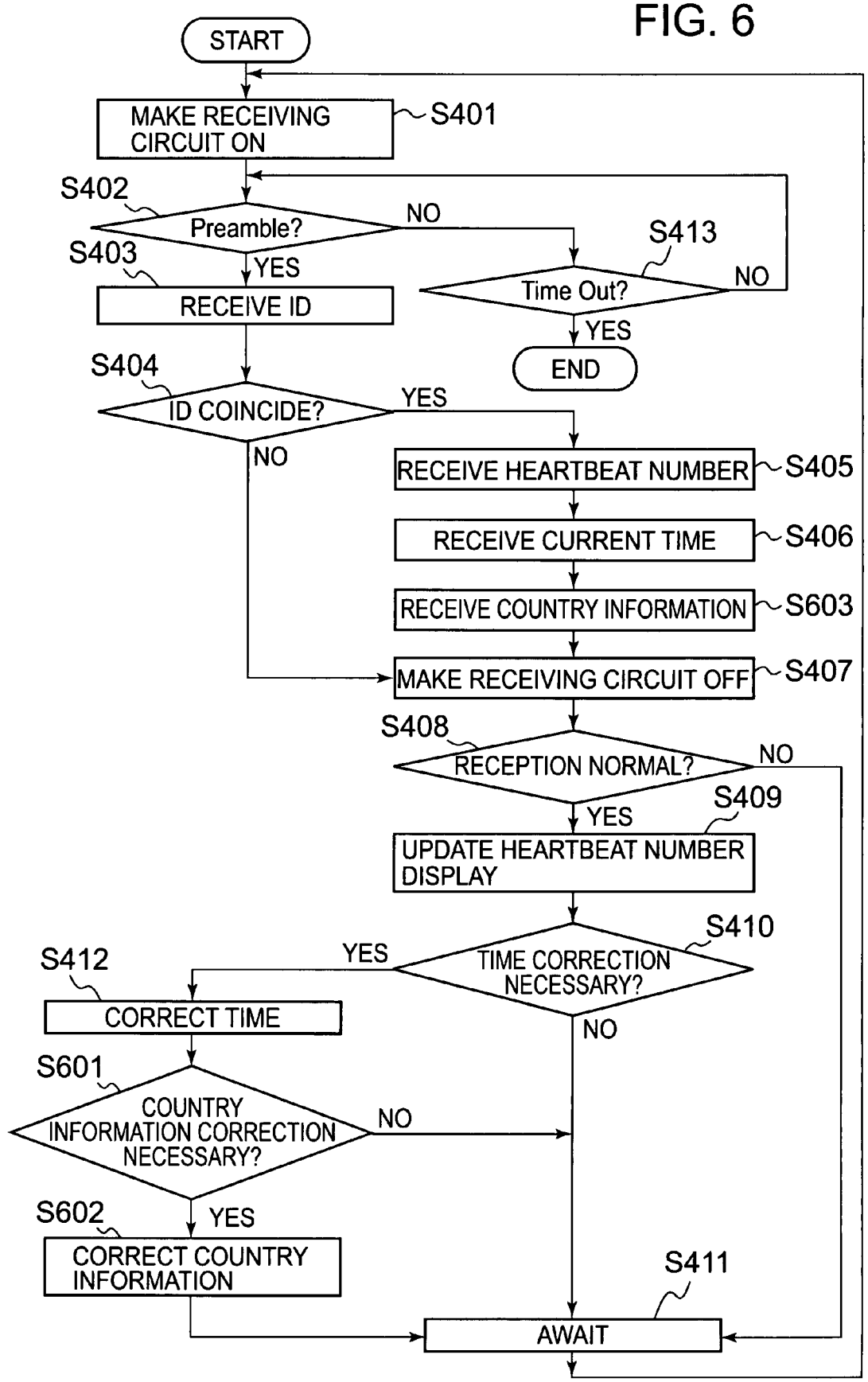
FIG. 6 is a flowchart showing a processing of a portable type information receiving apparatus according to a second embodiment of the invention.

FIG. 6 is a flowchart showing a processing of the portable type information receiving apparatus according to the second embodiment, and portions the same as those of FIG. 4 are attached with the same notations.

Figure 7:
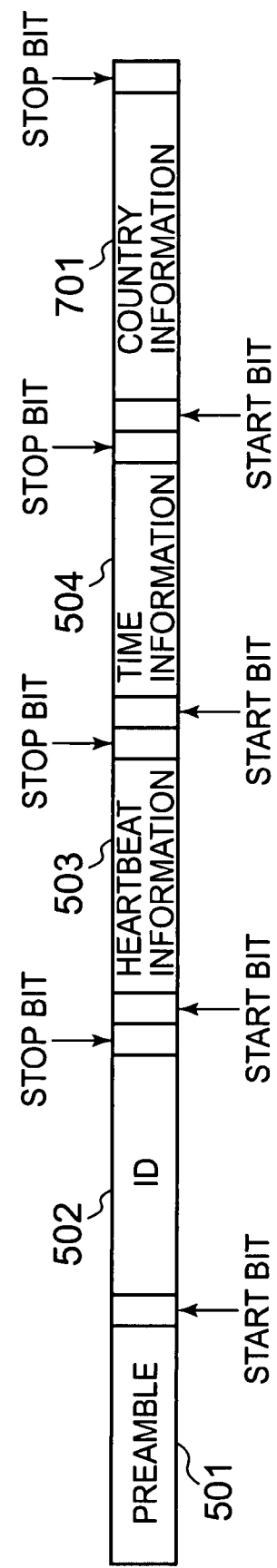
FIG. 7 is a diagram showing a style of a transmitting data used in a portable type information transmitting system according to the second embodiment of the invention.

FIG. 7 is a diagram showing a style of a transmitting data transmitted from the portable type information transmitting apparatus according to the second embodiment to the portable type information receiving apparatus, and portions the same as those of FIG. 5 are attached with the same notations. In FIG. 7, the transmitting data includes country information 701 for indicating by which country the current time information is constituted in addition to the information of FIG. 5.

Although according to the second embodiment, a hardware constitution of the portable type information transmitting apparatus is the same as that of FIG. 1, RAM 108 is stored with country determining reference information for determining a name of a country of the current time received, CPU 106 is constituted to determine the name of the country from a received standard radio wave based on the country determining reference information and generate to transmit the transmitting data of the style shown in FIG. 7.

Further, the name of the country can be determined from the standard radio wave based on a frequency and a code style of the radio wave, and therefore, a plurality of sets of tables corresponding the frequency of the standard radio wave and the code style and the country name may be stored as the country determining reference information.

Although a hardware constitution of the portable type information receiving apparatus is the same as that of FIG. 2, inside of RAM 205 is stored with country information included in the newest transmitting data received from the information transmitting apparatus.

Operation of the portable type information transmitting system according to the second embodiment will be explained as follows. Further, an explanation will mainly be given of a portion which differs from that of the first embodiment and an explanation will be omitted for the same portion.

CPU 106 of the information transmitting apparatus 100 generates the transmitting data of the style shown in FIG. 7 by synthesizing the country information 701 determined based on the country determining information stored to RAM 108 to the identification information 501, the heartbeat number 502, the current time 503 stored to RAM 108 when the calculated heartbeat number is a normal value, and when the transmission time reached by the predetermined period is reached, CPU 106 switches a tuning circuit of the switching circuit 111 for transmission and connects the antenna 112 to switch to a side of the transmitting circuit 109 to transmit to output the transmitting data.

On the other hand, on the side of the portable type information receiving apparatus 200, CPU 203 receives the country information at a processing step S603, corrects time at the processing step S412, thereafter, compares the received country information and the country information stored to RAM 205 to determine whether it is necessary to change the country information (step S601 of FIG. 6), when the received country information and the country information stored to RAM 205 differ from each other, CPU 203 corrects the country information of RAM 205 to the newly received country information, displays the country name in correspondence with a newly received country information on the display means 210 and proceeds to the processing step S411 (step S602).

When CPU 203 determines that it is not necessary to correct the country information at a processing step 601, CPU 203 proceeds to the processing step 411. Thereafter, a processing similar to the processing and the processing of FIG. 4 is repeated. Thereby, the display means 210 of the information receiving apparatus 200 is displayed with the heartbeat information, the current time information and the country information of the current time.

As described above, according to the second embodiment, not only an effect similar to that of the first embodiment is achieved but also an effect of capable of easily grasping in which country the apparatus is used is achieved since the country information is displayed on the display means 210 and the country information is corrected in accordance with the country in which the apparatus is used. Therefore, the apparatus can be used not only in Japan but also in a country using a standard radio wave for correcting time such as United States or the like.

Further, the portable type information transmitting apparatus according to the respective embodiments include the heartbeat measuring function and the radio wave timepiece function and achieve an effect of capable of easily grasping a variation in the heartbeat over time.

Further, although according to the embodiments, an explanation has been given of an example of the apparatus having the heartbeat measuring function as the portable information transmitting apparatus, the apparatus is applicable to an apparatus having a function of measuring bionic information such as an apparatus having a walk step number measuring function, an apparatus having a pulse be at measuring function or the like.

Further, although time and the heartbeat number are notified by the displaying means 210, the notification can variously be modified such that the notification is carried out by sound.

The invention is applicable to systems having various bionic information measuring functions of a heartbeat measuring function, a walk step number measuring function, a pulse be at measuring function and the like and a radio wave correcting function.

Further, the invention is applicable to a system utilized not only in Japan but also in a country using the standard radio wave for correcting the time such as United States.

What is claimed is:

1. A portable type information transmitting system comprising:
   portable type information transmitting means comprising bionic information measuring means for outputting bionic information in accordance with a detected bionic signal; radio wave receiving means for receiving a standard radio wave that includes current time information; first time counting means for counting time; first time correcting means for correcting the time counted by the first time counting means based on the current time information included in the standard radio wave received by the standard radio wave receiving means; transmission data generating means for generating transmission data including first time information corresponding to the time counted by the first time counting means and the bionic information from the bionic information measuring means; data transmitting means for transmitting the transmission data generated by the transmission data generating means; and mounting detecting means for detecting whether or not the bionic information measuring means is mounted to the body of a user; wherein when the mounting detecting means detects that the bionic information measuring means is not mounted to the body of the user, the radio wave receiving means receives the standard radio wave, and the first time correcting means corrects the time counted by the first time counting means based on the standard radio wave received by the radio wave receiving means; and
   portable type information receiving means comprising data receiving means for receiving the transmission data transmitted by the data transmitting means; second time counting means for counting time; second time correcting means for correcting time counted by the second time counting means based on the first time information in the transmitting data received by the data receiving means; and notifying means for notifying the time counted by the second time counting means and bionic data based on the bionic information included in the transmission data received by the data receiving means.

2. The portable type information transmitting system according to claim 1; wherein the portable information transmitting means further comprises first storing means for storing first identification information, and the transmission data generating means further generates a signal including the first identification information as the transmission data; wherein the portable type information receiving means further comprises second storing means for storing second identification information, and identification information determining means for determining whether the first and the second identification information are brought into a predetermined relationship; and wherein when the identification information determining means determines that the first and the second identification information are brought into the predetermined relationship, the second time correcting means corrects the time counted by the second time counting means based on the first time information included in the transmission data.

3. The portable type information transmitting system according to claim 2; wherein when the identification information determining means determines that the first and the second identification information are brought into the predetermined relationship, the notifying means notifies the bionic data based on the bionic information included in the transmission data.

4. The portable type information transmitting system according to claim 3; wherein the portable type information transmitting means further comprises country information generating means for generating country information based on the standard radio wave received by the radio wave receiving means; wherein the transmission data generating means further generates a signal that includes the country information of the transmission data and that is included in the transmission data transmitted by the transmission data generating means; and wherein the notifying means of the portable type information receiving means notifies the country information included in the transmission data.

5. The portable type information transmitting system according to claim 2; wherein the portable type information transmitting means further comprises country information generating means for generating country information based on the standard radio wave received by the radio wave receiving means; wherein the transmission data generating means further generates a signal that includes the country information of the transmission data and that is included in the transmission data transmitted by the transmission data generating means; and wherein the notifying means of the portable type information receiving means notifies the country information included in the transmission data.

6. The portable type information transmitting system according to claim 1; wherein the portable type information transmitting means further comprises country information generating means for generating country information based on the standard radio wave received by the radio wave receiving means; wherein the transmission data generating means further generates a signal that includes the country information of the transmission data and that is included in the transmission data transmitted by the transmission data generating means; and wherein the notifying means of the portable type information receiving means notifies the country information included in the transmission data.

7. A portable type information transmitting apparatus comprising: bionic information measuring means for outputting bionic information in accordance with a detected bionic signal; radio wave receiving means for receiving a standard radio wave that includes current time information; time counting means for counting time; time correcting means for correcting the time counted by the time counting means based on the standard radio wave received by the radio wave receiving means; transmission data generating means for generating transmission data including first time information corresponding to the time counted by the time counting means and the bionic information from the bionic information measuring means; data transmitting means for transmitting the transmission data generated by the transmission data generating means; and mounting detecting means for detecting whether or not the bionic information measuring means is mounted to the body of a user; wherein when the mounting detecting means detects that the bionic information measuring means is not mounted to the body of the user, the radio wave receiving means receives the standard radio wave, and the first time correcting means corrects the time counted by the first time counting means based on the standard radio wave received by the radio wave receiving means.

8. The portable type information transmitting apparatus according to claim 7; further comprising storing means for storing identification information; wherein the transmission data generating means further generates a signal including the identification information as the transmission data.

9. The portable type information transmitting apparatus according to claim 7; further comprising country information generating means for generating country information based on the standard radio wave received by the radio wave receiving means; wherein the transmission data generating means further generates a signal including the country information as the transmission data.

10. A portable information transmitting system comprising:
a portable information transmitting device comprising a bionic information measuring section that outputs bionic information in accordance with a detected bionic signal; a radio wave receiving section that receives a standard radio wave including current time information; a first time counting section that counts time; a first time correcting section that corrects the time counted by the first time counting section based on the current time information included in the standard radio wave received by the radio wave receiving section; a transmission data generating section that generates transmission data including first time information corresponding to the time counted by the first time counting section and the bionic information from the bionic information measuring section; a data transmitting section that transmits the transmission data generated by the data generating section; and a mounting detecting section that detects whether or not the bionic information measuring section is mounted to the body of a user; wherein when the mounting detecting section detects that the bionic information measuring section is not mounted to the body of the user, the radio wave receiving section receives the standard radio wave, and the first time correcting section corrects the time counted by the first time counting section based on the standard radio wave received by the radio wave receiving section; and a portable type information receiving device comprising a data receiving section that receives the transmission data transmitted by the data transmitting section; a second time counting section that counts time; a second time correcting section that corrects time counted by the second time counting section based on the first time information in the transmitting data received by the data receiving section; and a notifying section that notifies the time counted by the second time counting section and bionic data based on the bionic information included in the transmission data received by the data receiving section.

* * * * *